United States Patent [19]

Kita et al.

[11] Patent Number: 5,149,827

[45] Date of Patent: Sep. 22, 1992

[54] METHOD FOR HANDLING MALEIMIDES

[75] Inventors: Yuichi Kita, Akashi; Kazuo Kishino; Hiroko Ueda, both of Himeji, all of Japan

[73] Assignee: Nippon Shokubai Kagaku Kogyo Co., Ltd., Osaka, Japan

[21] Appl. No.: 638,620

[22] Filed: Jan. 8, 1991

[30] Foreign Application Priority Data

Jan. 10, 1990 [JP] Japan .................................. 2-1525
Mar. 12, 1990 [JP] Japan .................................. 2-57959
May 18, 1990 [JP] Japan ................................ 2-126969

[51] Int. Cl.$^5$ ............................ C07D 207/448
[52] U.S. Cl. ................................................ 548/548
[58] Field of Search ........................................ 548/548

[56] References Cited

FOREIGN PATENT DOCUMENTS 62-126167 6/1987 Japan .
62-143911 6/1987 Japan .
62-145062 6/1987 Japan .
2132854 6/1987 Japan .................................. 548/548
63-316767 12/1988 Japan .

Primary Examiner—David B. Springer
Attorney, Agent, or Firm—Omri M. Behr

[57] ABSTRACT

A method for handling a maleimide, which method comprises handling said maleimide in the presence of a stabilizer at a temperature exceeding the melting point thereof in a state kept in contact with a gas phase having a molecular oxygen content of not more than 10% by volume.

19 Claims, No Drawings

METHOD FOR HANDLING MALEIMIDES

BACKGROUND OF THE INVENTION

1. Field of the Invention

This invention relates to a method for handling maleimides. More particularly, it relates to a method for handling, as in the process of transportation and storage, maleimides fast in a molten state proofed against coloration. Still more particularly, it relates to a method for safely and easily handling maleimides in a state proofed against coloration and polymerization.

2. Description of the Prior Art

The maleimides are compounds which are useful as raw materials for resins, medicines, and agricultural pesticides.

Heretofore, the maleimides which are solid at normal room temperature have been generally handled in the form of powder, flakes, and tablets. The maleimides in such a form entrain minute particles of themselves. Particularly during the transportation of such solid maleimides, the maleimides undergo gradual comminution and give rise to minute maleimide particles in a large amount.

The maleimides themselves possess a property of stimulating the human body. Particularly when a maleimide in the form of a fine powder is inhaled by a man, it stimulates the nasal cavity and the throat of the man and compels him to cough or sneeze. When this maleimide powder is suffered to adhere to the skin of a man and remain thereon, it causes inflammation of the affected area of his skin. The maleimides possess this undesirable quality. A man engaging in the work of handling a maleimide containing minute particles of itself, therefore, must pay rigid attention to keeping his skin from contact with the maleimide to the fullest possible extent.

Enormous labors, therefore, are required for the purpose of precluding the occurrence of minute particles of a maleimide to the fullest possible extent during the transportation of the maleimide or for the purpose of removing minute particles from the maleimide after the transportation.

When a solid substance is transported, it is packed in paper bags, drums, or other similar containers prior to the transportation in most cases. When the solid substance is a maleimide in this case, a man engaging in the transportation inevitably exposes his body to the maleimide and consequently suffers from adhesion of minute particles of the maleimide to his skin.

An attempt at conveying a solid substance by a pipeline for the purpose of preventing the solid substance from contacting the human body is fundamentally difficult to implement. Since the solid substance in conveyance has the possibility of clogging the pipeline, for example, the particles of the solid substance are subject to exacting restrictions as to shape, size, and specific gravity in order for the solid substance to be safely conveyed.

Thus, it is only logical to conclude that the transportation or conveyance of a maleimide which is solid at normal room temperature entails numerous problems. The same thing holds good with respect to the method to be employed for the storage of a solid maleimide.

As means for the solution of the problems mentioned above, methods which reside in handling maleimides in process of transportation or storage in the form of a solution in acrylonitrile, styrene, or a (meth)acrylic acid ester have been disclosed in JP-A-62-162,1167(1987), JP-A-62-143,911(1987), JP-A-62-145,062(1987), and JP-A-63-(1988)-316,767. These method are free from the occurrence of minute particles of maleimides detrimental to the human body and, therefore, may well be called excellent means as compared with the method which handle maleimides in a solid state. When the maleimides are handled in the form of a highly concentrated solution, these methods require a high temperature for the reduction of solid maleimides into the solution. Since the solvent to be used for the solution is a compound which in itself possesses an ability to polymerize, the produced maleimide solution cannot be long retained intact at the elevated temperature. To be specific, the maleimide solution suffers the occurrence of impuries such as the polymer of the solvent itself and the copolymer of the solvent with the maleimide used as a solute. These impurities cause coloration of the solution. This solution in its unmodified form is subjected to adjustment of concentration and then, as a heatresistance improving agent for ABS resin, AAS resin, AS resin, or ACS resin, for example, used for copolymerization with a monomer destined to form such a resin. When the maleimide solution to be used in this case happens to be colored as described above, the finished product is inevitably colored and consequently degraded heavily in commodity value.

The conventional methods which handle maleimides in the form of a solid or a solution, therefore, hardly deserve to be called perfect means.

An object of this invention, therefore, is to provide a novel method for handling a maleimide.

Another object of this invention is to provide a method for safe and simple transportation or storage of a maleimide without any possibility of the maleimide producing minute particles of itself during the course of transportation or storage.

Yet another object of this invention is to provide a method for handling a maleimide in such a manner as to be prevented from coloration and allowed to retain its quality intact for a long time.

SUMMARY OF THE INVENTION

These objects are accomplished by a method for handling a maleimide, which method comprises handling said maleimide in the presence of a stabilizer at a temperature exceeding the melting point thereof in a state kept in contact with a gas phase having a molecular oxygen content of not more than 10% by volume.

These objects are further accomplished by a method for handling a maleimide, which method comprises melting the maleimide in the presence of a stabilizer at a temperature exceeding the melting point thereof in a state kept in contact with a gas phase having a molecular oxygen content of not more than 10% by volume, solidifying the resultant solution by cooling, and heating the resultant solid maleimide to a temperature exceeding the melting point thereof in the presence of the stabilizer in a state kept in contact with a gas phase having a molecular oxygen content of not less than 0.1% by volume thereby allowing the maleimide to be handled in a liquid state.

We have continued a diligent study for the purpose of developing a method for vesting a maleimide with thermal stability to resist coloration when the maleimide is dissolved not by the use of a solvent but by being heated at a temperature exceeding the melting point thereof and is consequently handled in a dissolved state or a liquid state, to find that the prevention of the maleimide from coloration aimed at by this invention is attained by repressing the molecular oxygen content of a gas phase enveloping the maleimide below a specific level. This invention has been perfected on the basis of this knowledge. When the maleimide is dissolved by being heated to a temperature exceeding the melting point thereof, packed in the molten state in a container, solidified by being cooled and then transported or stored in the solid state, and then put to use, the prevention of the maleimide from coloration aimed at is accomplished by again dissolving the solid maleimide under specific conditions. In this case, since the maleimide which is solid at normal room temperature is not required to be dissolved by the use of a solvent or by being heated to an elevated temperature in preparation for storage, it can be stored intact for a long time without any possibility of undergoing an alteration such as polymerization. Thus, this invention may well be regarded as a literally surprising advance in the art of handling maleimides.

The method of this invention, therefore, enjoys the following advantages.

(1) This method enables a maleimide which causes a strong stimulation in the human body to be handled not in a powdery state but in a liquid state and, therefore, allows safe and easy handling of the maleimide.

(2) It enables the maleimide to be stored long in the liquid state without a sacrifice of its high quality.

(3) When the maleimide stored in the liquid state is used in the production of a polymer, the finished product shows virtually no sign of coloration and enjoys high quality.

(4) When the redissolved maleimide is used in the production of a polymer, the finished product shows virtually no sign of coloration and enjoys high quality.

EXPLANATION OF THE PREFERRED EMBODIMENT

Now, this invention will be described more specifically below.

The maleimides which are effectively handled as in transportation or storage by the method of this invention include N-methyl maleimide, N-ethyl maleimide, N-hexyl maleimide, N-octyl maleimide, N-dodecyl maleimide, N-benzyl maleimide, N-cyclohexyl maleimide, N-phenyl maleimide, N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, and N-tribromophenyl maleimide, for example. These are not the only maleimides for which this invention can be utilized.

The stabilizers which are effectively usable in the handling of a maleimide at a temperature exceeding the melting point thereof include methoxybenzoquinone; p-methoxyphenol; phenothiazine; hydroquinone; diphenyl amines; methylene blue; zinc dimethyldithiocarbamate; dialkyldithiocarbamates such as copper dimethyldithiocarbamate and copper dibutyldithiocarbamate; copper salicylate; thiodipropionic esters; mercaptobenzimidazole; alkyl-substituted hydroxybenzenes and alkylbisphenols; hindered phenols; phosphoric esters; phosphorous esters; and phosphoric acid amide, for examples. These are not the only stabilizers which are available herein. These stabilizers may be used either singly or as a mixture of two or more members.

Particularly, at least one stabilizer selected from the group consisting of alkyl-substituted hydroxybenzenes, thiodipropionic esters, hindered phenols, phosphoric esters, phosphorous esters, and phosphoric acid amide is highly effective in preventing a maleimide from coloration at a temperature exceeding the melting point of the maleimide. Thus, these stabilizers are advantageously used in this invention.

The use of at least one alkyl-substituted hydroxybenzene in combination with at least one phosphorus compound selected from the group consisting of phosphoric esters, phosphorous esters, and phosphoric acid amide as a stabilizer brings about an outstanding effect in the prevention of a maleimide from coloration.

The alkyl-substituted hydroxybenzenes which are effectively usable as a stabilizer in this invention include 2,4-dimethyl-6-tert-butyl phenol, 4-tert-butyl catechol, 2,5-di-tert-butyl hydroquinone, 2-tert-dibutyl hydroquinone, 4,4'-thio-bis(6-tert-butyl-m-cresol, 2,4-bis(n-octylthio)-6-(4-hydroxy-3,5-di-t-butyl anilino)-1,3,5-triazine, 2,2'-thio-bis(4-methyl-6-t-butyl phenyl), triethylene glycol-bis(3-(3-t-butyl-5-methyl-4-hydroxy phenol)propionate), pentaerythrityl-tetra-kis(3-(3,5-di-t-butyl-4-hydroxy phenyl)propionate), octadecyl-3-(3,5-di-t-butyl-4-hydroxyphenyl)propionate, 2,2-thio-diethylene bis(3-(3,5-di-t-butyl-4-hydroxyphenyl)propionate), 1,6-hexane diol-bis(3-(3,5-di-t-butyl-4-hydroxyphenyl)propionate), tris-(3,5-di-ti-butyl-4-hydroxybenzyl)-isocyanurate, 1,3,5-trimethyl-2,4,6-tris(3,5-di-t-butyl-4-hydroxybenzyl)benzene, N,N'-hexamethylene-bis(3,5-di-t-butyl-4-hydroxy-hydrocinnamide), and 3,5-di-t-butyl-4-hydroxy-benzyl phosphonate diethyl ester, for example. Among other stabilizers cited above, 2,4-dimethyl-6-tert-butyl phenol, 4-tert-butyl catechol, 2,5-di-tert-butyl hydroquinone, 2-tert-dibutyl hydroquinone, 4,4'-thio-bis(6-tert-butyl-m-cresol), 2,4-bis(n-octylthio)-6-(4-hydroxy-3,5-di-t-butyl anilino)-1,3,5-triazine, 2,4'-thio-bis-(4-methyl-6-t-butyl phenol), and triethylene glycol-bis-(3-(3-t-butyl-5-methyl-4-hydroxyphenyl)propionate) are advantageously usable herein because they are excellent effective in preventing a maleimide from coloration and from polymerization.

The thio-dipropionic esters which are effectively usable in this invention include ditridecyl-3,3'-thiodipropionate, dilauryl-3,3'-thiopropionate, ditetradecyl-3,3'-thiodipropionate, distearyl-3,3'-thiodipropionate, and dioctyl-3,3'-thiodipropionate, for example. These are not the only thio-dipropionic esters which are available herein.

The hindered phenols which are effectively usable herein include 2,4-bis(n-octylthio)-6-(4-hydroxy-3,5-di-t-butylanilino)-1,3,5-triazine, 2,2'-thiobis-(4-methyl-6-t-butyl phenol), triethylene glycol bis-(3-(3-t-butyl-5-methyl-4-hydroxyphenyl)propionate), pentaerythrityl-tetrakis(3-(3,5-di-t-butyl-4-hydroxyphenyl)propionate), octadecyl-3-(3,5-di-t-butyl-4-hydroxyphenyl)propionate, 2,2-thio-diethylene-bis(3-(3,5-di-t-butyl-4-hydroxyphenyl)propionate), 1,6-hexane diol-bis(3-(3,5-di-t-butyl-4-hydroxyphenyl)propionate), tris-(3,5-di-t-butyl-4-hydroxybenzyl)-isocyanurate, 1,3,5-trimethyl-2,4,6-tris(3,5-di-t-butyl-4-hydroxybenzyl)benzene, N,N'-hexamethylene-bis( 3,5-di-t-butyl-4-hydroxy-hydrocinnamide), and 3,5-di-t-butyl-4-hydroxy-benzyl phosphonate-diethyl ester, for example. Among other hindered phenols cited above, 2,4-bis(n-aoctylthio)-6-(4-hydroxy-3,5-t-butyl anilino)-1,3,5-triazine, 2,2'-thiobis-(4-methyl- 6-t-butyl phenyl, and triethylene glycol-bis(3-(3-t-butyl-5-methyl-4-hydroxyphenyl)propionate) are advantageously usable herein. These are not the only hindered phenols which are available herein.

The phosphorous esters which are effectively usable in the present invention include triphenyl phosphite, tris(nonylphenyl) phosphite, triethyl phosphite, tris(2-ethylhexyl) phosphite, tridecyl phosphite, tris(tridecyl) phosphite, tristearyl phosphite, diphenyl mono(2-ethylhexyl) phoslphite, diphenyl monodecyl phosphite, diphenyl monodecyl phospite, dilauryl hydrogen phosphite, dilauryl hydrogen phosphite, diphenyl hydrogen phosphite, tetraphenyl dipropylene glycol diphosphite, tetraphenyl tetra(tridecyl) pentaerythritol tetraphosphite, tetra(tridecyl)-4,4'-isopropylidene diphenyl phosphite, trilauryl trithiophosphite, bis(tridecyl)pentaerythritol phosphite, bis(nonylphenyl)pentaerythritol diphosphite, distearylpentaerythritol diphosphite, tris(2,4-di-tertiary butylphenyl)phosphite, water-soluble bisphenol A, pentaerythritol phosphite polymer hydrated phosphenol A, and phosphite polymer, for example. These are not the only phosphorous esters which are available herein.

The phosphoric esters and other phosphorus compounds which are effectively usable in this invention include hexamethyl phosphoric triamide, ethyldiethyl phosphonoacetate, ethyl acid phosphate, $\beta$-chloroethyl acid phosphate, butyl acid phosphate, butyl pyrophosphate, butoxyethyl acid phosphate, 2-ethylhexyl acid phosphate, di(2-ethylhexyl) phosphate, ethylene glycol acid phosphate, d(2-hydroxyethyl) methacrylate acid phosphate, tris(2-chloroethyl) phosphate, tris(dichloropropyl)phosphate, octyl dichloropropyl phosphate, phenyl dichloropropyl phosphate, trimethyl phosphate, triethyl phosphate, tributyl phosphate, trioctyl phosphate, tricresyl phosphate, and triphenyl phosphate, for example. These are not the only phosphoric esters and phosphorus compounds which are available herein.

The phosphoric acid amides which are effectively usable in this invention include hexamethyl phosphoric triamide, for example.

Among the phosphorus compounds cited above, at least one member selected from the group consisting of tris(2-chloroethyl) phosphate, tris-nonylphenyl phosphite, tristearyl phosphite, distearyl pentaerythritol diphosphite, and hexamethyl phosphoric triamide can be used advantageously.

The effect which the above mentioned stabilizer manifests in preventing a maleimide from polymerization is conspicuous as compared with that which is manifested by p-methoxyphenol or hydroquinone conventionally used as a polymerization inhibitor, as clearly demonstrated in the working examples and controls to be cited herein below.

The amount of the stabilizer to be used in this invention is in the range of 0.0001 to 1.0% by weight, preferably 0.001 to 0.1% by weight. The kind of the stabilizer to be used herein is selected in due consideration of the kind of the polymer to be produced, the method of polymerization, the initiator to be used, for example. When an alkyl-substituted hydroxybenzene and a phosphorus compound are jointly used, though the ratio of these two compounds is not specifically defined, the gravimetric ratio of the alkyl-substituted hydroxybenzene to the phosphorus compound is desired to be in the range of 1:0.1 to 1:1000, preferably 1:1 to 1:100.

When a maleimide particularly in a granular or powdery form is to be handled as heated to a temperature exceeding the melting point thereof, the method of this invention requires this maleimide to be handled as held in contact with a gas phase having a molecular oxygen content of not more than 10% by volume. In accordance with our knowledge, a definite relation exists between the coloration of a maleimide and the molecular oxygen content in the gas phase enveloping the maleimide being handled. In the normal atmosphere of air, the maleimide is colored at a notably high speed. Particularly in the absence of a stabilizer and in an atmosphere having a high molecular oxygen content, this coloration is accelerated. When the maleimide is handled at a temperature exceeding the melting point thereof, the repression of the molecular oxygen content in the gas phase below the level of 10% by volume is effective in preventing the maleimide from coloration. The desirability of the result of handling increases in proportion as this concentration decreases. Particularly when the gas phase containing such an inert gas as nitrogen, carbon dioxide, or argon, the handling can be conveniently effected. In the gas phase, however, the molecular oxygen is preferable to be present in a concentration of at least 0.1% by volume. The concentration of the molecular oxygen present in the gas phase, therefore, is desired to be in the range of 0.1 to 10% by volume.

When the maleimide which has been dissolved as described above, then cooled until solidification, and stored or transported is put to use, the solid maleimide is handled still more effectively by being heated until liquefaction in the presence of the aforementioned stabilizer at a temperature exceeding the melting point thereof in a state kept in contact with a gas phase having a molecular oxygen content of not less than 0.1% by volume.

The method just described is carried out generally in a hermetically sealed vessel. This hermetically sealed vessel is only required to be provided with a heating part and may be in any desired shape. The hermetically sealed vessels which are effectively usable herein include stationary tanks such as tanks furnished with an inner heating coil and tanks furnished with a heating jacket and mobile tanks such as tank cars, tank lorries, and bulk containers, for example.

A given maleimide is placed in a molten state in the hermetically sealed vessel. Though no specific condition is imposed on the work of placing the maleimide in the vessel, the liquid maleimide is preferable to have the aforementioned stabilizer incorporated therein in advance of the entry in the vessel. Inside the hermetically sealed vessel, the liquid maleimide is solidified by either spontaneous cooling or forced external cooling. Prior to use, the maleimide which has been solidified as described above and then transported or stored is heated until liquefaction. Then, the maleimide is handled in the resultant liquid state.

In a preferred embodiment of this invention, a maleimide in a molten state is placed in a mobile tank such as a tank lorry or a bulk container, solidified therein, transported in the resultant solid state to a destination, heated there until liquefaction with a heating device annexed to the tank, and handled in the resultant liquid state.

A definite relation exists between the coloration and polymerization which occur in a maleimide during the application of heat for liquefaction and the molecular oxygen content in the gas phase enveloping the maleimide. The maleimide quickly polymerizes if the molecular oxygen content of the gas phase is less than 0.1% by volume. This polymerization is accelerated when the heating is carried out in the absence of the stabilizer and the molecular oxygen content is less than 0.1% by volume. It has been found that the polymerization tends to be repressed but the coloration tends to be encouraged when the molecular oxygen content is increased. For the method of this invention to yield good results, the molecular oxygen content in the gas phase is required to exceed 0.1% by volume and desired to be not less than 0.1% by volume and not more than 10% by volume, preferably to be in the range of 1 to 8% by volume. Still more desirable results are obtained when the gas phase is displaced with such an inert gas as nitrogen, carbon dioxide, or argon.

The temperature at which the molten maleimide is handled is to exceed the melting point of the maleimide. From the viewpoint of minimizing the coloration, this temperature is selected in the range lower by 1° to 50° C., preferably 5° to 20° C., than the melting point of the maleimide.

Now, the present invention will be described more specifically below with reference to working examples.

EXAMPLES 1 TO 35 AND CONTROLS 1 TO 3

In a hermetically sealable stainless steel vessel, a various maleimide and a various stabilizer metered out in various amounts were placed and, in a gas phase having a various molecular oxygen content, heated as immersed in an oil bath kept at a prescribed temperature. In this case, the gas phase was displaced with nitrogen gas so as to adjust the molecular oxygen content thereof to a stated level. After the elapse of a varying period in the range of one to three months, the vessel was removed from the oil bath and the solution consequently formed therein was visually examined as to the appearance. The maleimide resulting from the heating was subjected to solution polymerization with styrene and the produced polymer was visually examined as to the appearance. The results are shown in Table 1 (the data of effects of alkyl-substituted hydroxybenzenes used as stabilizer), Table 2 (the data of effects of thiodipropionic esters used as stabilizer), Table 3 (the data of effects of hindered phenols used as stabilizer), and Table 4 (the data for comparison).

TABLE 1

| Example No. | Maleimides | Stabilizer | Amount of stabilizer (ppm) | Conc. of $O_2$ in gas phase (vol %) | Temperature (°C.) | Duration of heating (month) | Appearance of maleimide before heating | Appearance of maleimide after heating | Appearance of polymer |
|---|---|---|---|---|---|---|---|---|---|
| 1 | N-phenyl maleimide | 2,4-dimetyl-6-t-butyl phenol | 100 | 0.1 | 100 | 3 | yellowish transparent | yellowish transparent | white |
| 2 | N-phenyl maleimide | 2,4-dimetyl-6-t-butyl phenol | 100 | 2 | 110 | 3 | yellowish transparent | yellowish transparent | white |
| 3 | N-phenyl maleimide | 4-t-butyl cathecol | 100 | 2 | 110 | 3 | yellowish transparent | yellowish transparent | white |
| 4 | N-phenyl maleimide | 4,4'-thiobis (6-t-butyl-m-cresol) | 100 | 2 | 110 | 3 | yellowish transparent | yellowish transparent | white |
| 5 | N-methyl maleimide | 4-t-butyl cathecol | 100 | 2 | 105 | 3 | colorless transparent | colorless transparent | white |
| 6 | N-dodecyl maleimide | 4-t-butyl cathecol | 100 | 2 | 70 | 3 | colorless transparent | colorless transparent | white |
| 7 | N-cyclohexyl maleimide | 4-t-butyl cathecol | 100 | 2 | 100 | 3 | colorless transparent | colorless transparent | white |
| 8 | N-o-chloro phenyl maleimide | 4-t-butyl cathecol | 100 | 2 | 80 | 3 | slightly yellowish transparent | slightly yellowish transparent | white |
| 9 | N-o-methyl phenyl maleimide | 4-t-butyl cathecol | 100 | 2 | 80 | 3 | slightly yellowish transparent | slightly yellowish transparent | white |
| 10 | N-phenyl maleimide | 4-t-butyl cathecol | 10 | 2 | 80 | 3 | yellowish transparent | yellowish transparent | white |
| 11 | N-phenyl maleimide | 4-t-butyl cathecol | 1000 | 2 | 100 | 3 | yellowish transparent | yellowish transparent | white |
| 12 | N-phenyl maleimide | 4-t-butyl cathecol | 100 | 10 | 100 | 3 | yellowish transparent | yellowish transparent | white |

TABLE 2

| Example No. | Maleimides | Stabilizer | Amount of stabilizer (ppm) | Conc. of $O_2$ in gas phase (vol %) | Temperature (°C.) | Duration of heating (month) | Appearance of maleimide before heating | Appearance of maleimide after heating | Appearance of polymer |
|---|---|---|---|---|---|---|---|---|---|
| 13 | N-phenyl maleimide | ditridecyl-3,3'-thiodipropionate | 100 | 0.1 | 100 | 3 | yellowish transparent | yellowish transparent | white |
| 14 | N-phenyl maleimide | ditridecyl-3,3'-thiodipropionate | 100 | 2 | 110 | 3 | yellowish transparent | yellowish transparent | white |
| 15 | N-phenyl maleimide | dilauryl-3,3' thiodipropionate | 100 | 2 | 110 | 3 | yellowish transparent | yellowish transparent | white |
| 16 | N-methyl maleimide | distearyl-3,3'-thiodipropionate | 100 | 2 | 105 | 3 | colorless transparent | colorless transparent | white |
| 17 | N-dodecyl maleimide | distearyl-3,3'-thiodipropionate | 100 | 2 | 70 | 3 | colorless transparent | colorless transparent | white |
| 18 | N-cyclohexyl maleimide | distearyl-3,3'-thiodi- | 100 | 2 | 100 | 3 | colorless transparent | colorless transparent | white |

TABLE 2-continued

| Example No. | Maleimides | Stabilizer | Amount of stabilizer (ppm) | Conc. of $O_2$ in gas phase (vol %) | Temperature (°C.) | Duration of heating (month) | Appearance of maleimide before heating | Appearance of maleimide after heating | Appearance of polymer |
| --- | --- | --- | --- | --- | --- | --- | --- | --- | --- |
| 19 | N-o-chloro phenyl maleimide | distearyl-3,3'-thiodi-propionate | 100 | 2 | 80 | 3 | slightly yellowish transparent | slightly yellowish transparent | white |
| 20 | N-o-methyl phenyl maleimide | distearyl-3,3'-thiodi-propionate | 100 | 2 | 80 | 3 | slightly yellowish transparent | slightly yellowish transparent | white |
| 21 | N-phenyl maleimide | distearyl-3,3'-thiodi-propionate | 10 | 2 | 80 | 3 | yellowish transparent | yellowish transparent | white |
| 22 | N-phenyl maleimide | distearyl-3,3'-thiodi-propionate | 1000 | 2 | 100 | 3 | yellowish transparent | yellowish transparent | white |
| 23 | N-phenyl maleimide | distearyl-3,3'-thiodi-propionate | 100 | 10 | 100 | 3 | yellowish transparent | yellowish transparent | white |

TABLE 3

| Example No. | Maleimides | Stabilizer | Amount of stabilizer (ppm) | Conc. of $O_2$ in gas phase (vol %) | Temperature (°C.) | Duration of heating (month) | Appearance of maleimide before heating | Appearance of maleimide after heating | Appearance of polymer |
| --- | --- | --- | --- | --- | --- | --- | --- | --- | --- |
| 24 | N-phenyl maleimide | 2,2'-thiobis(4-methyl-6-t-butyl phenol) | 100 | 0.1 | 100 | 3 | yellowish transparent | yellowish transparent | white |
| 25 | N-phenyl maleimide | 2,2'-thiobis(4-methyl-6-t-butyl phenol) | 100 | 2 | 110 | 3 | yellowish transparent | yellowish transparent | white |
| 26 | N-phenyl maleimide | BOHT | 100 | 2 | 110 | 3 | yellowish transparent | yellowish transparent | white |
| 27 | N-phenyl maleimide | TGBP | 100 | 2 | 110 | 3 | yellowish transparent | yellowish transparent | white |
| 28 | N-methyl maleimide | " | 100 | 2 | 105 | 3 | colorless transparent | colorless transparent | white |
| 29 | N-dodecyl maleimide | " | 100 | 2 | 70 | 3 | colorless transparent | colorless transparent | white |
| 30 | N-cyclohexyl maleimide | " | 100 | 2 | 100 | 3 | colorless transparent | colorless transparent | white |
| 31 | N-o-chloro phenyl maleimide | " | 100 | 2 | 80 | 3 | slightly yellowish transparent | slightly yellowish transparent | white |
| 32 | N-o-methyl phenyl maleimide | " | 100 | 2 | 80 | 3 | slightly yellowish transparent | slightly yellowish transparent | white |
| 33 | N-phenyl maleimide | " | 10 | 2 | 80 | 3 | yellowish transparent | yellowish transparent | white |
| 34 | N-phenyl maleimide | " | 1000 | 2 | 100 | 3 | yellowish transparent | yellowish transparent | white |
| 35 | N-phenyl maleimide | " | 100 | 10 | 100 | 3 | yellowish transparent | yellowish transparent | white |

TABLE 4

| Control No. | Maleimides | Stabilizer | Amount of stabilizer (ppm) | Conc. of $O_2$ in gas phase (vol %) | Temperature (°C.) | Duration of heating (month) | Appearance of maleimide before heating | Appearance of maleimide after heating | Appearance of polymer |
| --- | --- | --- | --- | --- | --- | --- | --- | --- | --- |
| 1 | N-phenyl maleimide | none | 0 | 2 | 100 | 1 | yellowish transparent | orange resin | — |
| 2 | N-phenyl maleimide | 4-t-butyl cathecol | 100 | 15 | 100 | 3 | yellowish transparent | orange transparent | slight yellow |
| 3 | N-phenyl maleimide | 4-t-butyl cathecol | 100 | 21 | 100 | 3 | yellowish transparent | slightly brownish transparent | slight yellowish brown |

EXAMPLES 36 TO 47

In a test tube, a various maleimide and a various stabilizer in varying amounts were sealed in and heated as immersed in an oil bath at 150° C. for three hours (all of maleimides were molten state). In this case, nitrogen gas was used to form the gas phase (with the molecular oxygen content adjusted to 5% by volume) in the test tube). After the three hours' heating, the sealed test tube was removed from the oil bath. The maleimide in the sealed test tube was cooled and pulverized and then analyzed by high-speed liquid chromatography to determine purity. The results are shown in Table 5.

EXAMPLE 48

In a stainless steel vessel measuring 10 cm in diameter and 20 cm in height and provided with a heating jacket, 1 kg of yellow N-phenyl maleimide having a purity of 99.8 f % by weight and 0.1 g of distearyl pentaerythritol diphosphite were heated to a temperature of 100° C. with the heat applied thereto through the jacket. In this case, the N-phenyl maleimide was a yellow liquid. The gas phase in the vessel was displaced with nitrogen gas (with the molecular oxygen content adjusted to 8% by volume).

The contents of the vessel were kept in the existent state for 30 days. At the end of the 30 days' standing, the N-phenyl maleimide was found to be still retaining its original yellow color. On analysis by high-speed liquid chromatography, it was found to possess a purity of 99.6% by weight, a value representing practically no change from the original purity.

EXAMPLES 48 TO 61

In a hermetically sealable stainless steel vessel, a various maleimide and a various stabilizer in varying amounts were placed and, in a gas phase having a various molecular oxygen content, heated as immersed in an oil bath kept at a prescribed temperature. In this case, the gas phase in the vessel was displaced with nitrogen gas with the molecular oxygen content therein adjusted to a stated level. After the elapse of three months, the vessel was removed from the oil bath and the solution consequently formed therein was visually examined as to the appearance. The maleimide resulting from the heating was subjected to solution polymerization with styrene. The produced polymer was visually examined as to the appearance. The results are shown in Table 6.

TABLE 5

| Example No. | Maleimide | Stabilizer | Amount of stabilizer (ppm) | Purity before heating (wt. %) | Purity after heating (wt. %) | Appearance before heating | Appearance after heating |
|---|---|---|---|---|---|---|---|
| 36 | N-phenyl maleimide | tris(2-chloroethyl) phosphate | 100 | 99.8 | 99.5 | yellow crystal | yellow crystal |
| 37 | N-phenyl maleimide | distearyl pentaerithritol diphosphite | 100 | 99.8 | 99.6 | " | " |
| 38 | N-phenyl maleimide | tris nonylphenyl phosphite | 100 | 99.8 | 99.6 | " | " |
| 39 | N-phenyl maleimide | tristearyl phosphite | 100 | 99.8 | 99.6 | " | " |
| 40 | N-methyl maleimide | distearyl pentaerithritol diphosphite | 100 | 99.8 | 99.6 | white crystal | white crystal |
| 41 | N-dodecyl maleimide | distearyl pentaerithritol diphosphite | 100 | 98.7 | 98.3 | " | " |
| 42 | N-cyclohexyl maleimide | distearyl pentaerithritol diphosphite | 100 | 99.5 | 99.2 | " | " |
| 43 | N-o-chloro phenyl maleimide | distearyl pentaerithritol diphosphite | 100 | 98.9 | 98.6 | slightly yellow crystal | slightly yellow crystal |
| 44 | N-o-methyl phenyl maleimide | distearyl pentaerithritol diphosphite | 100 | 99.5 | 99.3 | slightly yellow crystal | slightly yellow crystal |
| 45 | N-phenyl maleimide | distearyl pentaerithritol diphosphite | 10 | 99.8 | 99.0 | yellow crystal | yellow crystal |
| 46 | N-phenyl maleimide | distearyl pentaerithritol diphosphite | 1000 | 99.8 | 99.6 | " | " |
| 47 | N-phenyl maleimide | distearyl pentaerithritol diphosphite | 10000 | 99.8 | 99.6 | " | " |

TABLE 6

| Example No. | Maleimide | Stabilizer (1) | Stabilizer (2) | Amount of stabilizer (1) (ppm) | Amount of stabilizer (2) (ppm) | Conc. of O₂ in gas phase (vol %) | Temperature (°C.) | Duration of heating (month) | Appearance of maleimide before heating | Appearance of maleimide after heating | Appearance of polymer |
|---|---|---|---|---|---|---|---|---|---|---|---|
| 48 | N-phenyl maleimide | 4-t-butyl cathecol | tris(2-chloroethyl) phosphate | 100 | 500 | 0.1 | 100 | 3 | yellowish transparent | yellowish transparent | white |
| 49 | N-phenyl maleimide | 4,4'-thiobis (6-t-butyl-m-cresol) | trisnonyl phenol phosphite | 100 | 500 | 5 | 110 | 3 | yellowish transparent | yellowish transparent | white |
| 50 | N-phenyl maleimide | 2,5-di-t-butyl hydroquinone | pentaerithritol diphosphite | 100 | 500 | 5 | 110 | 3 | yellowish transparent | yellowish transparent | white |
| 51 | N-phenyl maleimide | BOHT (*) | pentaerithritol diphosphite | 1000 | 3000 | 5 | 110 | 3 | yellowish transparent | yellowish transparent | white |
| 52 | N-phenyl maleimide | TGBP (**) | pentaerithritol diphosphite | 1000 | 3000 | 5 | 110 | 3 | yellowish transparent | yellowish transparent | white |
| 53 | N-methyl maleimide | 4-t-butyl cathecol | pentaerithritol diphosphite | 100 | 500 | 5 | 105 | 3 | yellowish transparent | yellowish transparent | white |
| 54 | N-dodecyl maleimide | 4-t-butyl cathecol | pentaerithritol diphosphite | 100 | 500 | 5 | 70 | 3 | colorless transparent | colorless transparent | white |
| 55 | N-cyclohexyl maleimide | 4-t-butyl cathecol | pentaerithritol diphosphite | 100 | 500 | 5 | 100 | 3 | colorless transparent | colorless transparent | white |
| 56 | N-o-chloro phenyl | 4-t-butyl cathecol | pentaerithritol thritol | 100 | 500 | 5 | 80 | 3 | colorless transparent | colorless transparent | white |

TABLE 6-continued

| Example No. | Maleimide | Stabilizer (1) | Stabilizer (2) | Amount of stabilizer (1) (ppm) | Amount of stabilizer (2) (ppm) | Conc. of $O_2$ in gas phase (vol %) | Temperature (°C.) | Duration of heating (month) | Appearance of maleimide before heating | Appearance of maleimide after heating | Appearance of polymer |
|---|---|---|---|---|---|---|---|---|---|---|---|
| 57 | N-o-methyl phenyl maleimide | 4-t-butyl cathecol | pentaerithritol diphosphite | 100 | 500 | 5 | 80 | 3 | slightly yellowish transparent | slightly yellowish transparent | white |
| 58 | N-phenyl maleimide | 4-t-butyl cathecol | pentaerithritol diphosphite | 100 | 500 | 5 | 80 | 3 | slightly yellowish transparent | slightly yellowish transparent | white |
| 59 | N-phenyl maleimide | 4-t-butyl cathecol | pentaerithritol diphosphite | 10 | 100 | 5 | 100 | 3 | yellowish transparent | yellowish transparent | white |
| 60 | N-phenyl maleimide | 4-t-butyl cathecol | pentaerithritol diphosphite | 1000 | 3000 | 5 | 110 | 3 | yellowish transparent | yellowish transparent | white |
| 61 | N-phenyl maleimide | 4-t-butyl cathecol | pentaerithritol diphosphite | 100 | 500 | 10 | 110 | 3 | yellowish transparent | yellowish transparent | white |

(*) BOHT: 2,4-bis(n-octylthio)-6-(hydroxy-3,5-di-t-butylanilino)-1,3,5-triazine
(**) TGBP: triethylene glycol-bis-[3-(3-t-butyl-5-methyl-4-hydroxyphenyl)propionate]

EXAMPLE 62

A hermetically sealable cylindrical tank (5.6 m in length, 2.2 m in inside diameter, and 20 m³ in inner volume) provided with a heating part was charged with 18 tons of molten N-phenyl maleimide having a purity of 99.6% by weight and containing 0.01% by weight of triethylene glycol bis-[3-(3-t-butyl-5-methyl-4-hydroxyphenyl) propionate] and 0.05% by weight of tristearyl phosphite each as a stabilier. Thereafter, the gas phase in the tank was displaced with nitrogen gas so as to acquire a molecular oxygen content of 5% by volume and the liquid phase was solidified by spontaneous cooling.

After the contents of the tank were retained in the existent state for one month, they were melted again by passing steam at 110° C. through the heating part. The resultant solution was found to be a yellow transparent liquid showing no sign of the occurrence of polymerization. On analysis by liquid chromatography, this solution was found to possess a purity of 99.6%, a value indicating perfect absence of change. When the same N-phenyl maleimide and styrene were subjected to solution polymerization by the procedure described in Referential Example, there was obtained a white polymer showing no sign of coloration.

EXAMPLE 63

The procedure of Example 62 was faithfully repeated, except that 0.005% by weight of 4-tert-butyl catechol and 0.05% by weight of distearyl pentaerythritol diphosphite were used instead as stabilizers and the molecular oxygen content in the gas phase was adjusted by nitrogen gas displacement to 10% by volume. When the produced N-phenyl maleimide was melted again, there was obtained a yellow clear liquid showing no sign of polymerization. The results were perfectly equal to those obtained in Example 62.

REFERENTIAL EXAMPLE (SYNTHESIS OF POLYMER)

A four-necked flask having an inner volume of 1 liter and provided with a stirrer, a reflux condenser, a nitrogen gas inlet, and a dropping funnel was charged with 44 g of methylethyl ketone. The flask, with the gas phase therein thoroughly displaced with nitrogen, was heated to 80° C. To the methylethyl ketone kept heated at an inner temperature of 80° C., a mixed solution comprising of 96.55 g of N-phenyl maleimide, 58.07 g of styrene, and 460 g of methylethyl ketone and a solution consisting of 0.77 g of azoisobutylonitrile and 11 g of methylethyl ketone both prepared separately were added dropwise over a period of four hours. The resultant mixture was continuously stirred for one hour. Then, the reaction product consequently formed was cooled and transferred into two liters of methanol, separated by filtration, and dried, to obtain 147.8 g of a polymer. This polymer was a white powdery substance and was found to possess a molecular weight of 100,000 (by GPC analysis). Polymers were synthesized by following the same procedure, excepting the molar ratio of a varying maleimide to styrene was fixed at 1 and the amount of azoisobutylonitrile was fixed at 0.5% by weight based on the amount of monomer. These polymers were evaluated as to appearance.

What is claimed is:

1. A method for handling a maleimide, which method comprises handling said maleimide in the presence of a stabilizer at a temperature exceeding the melting point thereof in a state kept in contact with a gas phase having a molecular oxygen content of not more than 10% by volume.

2. A method according to claim 1, wherein said stabilizer is at least one compound selected from the group consisting of alkyl-substituted hydroxybenzenes, thiodipropionic esters, hindered phenols, phosphoric esters, phosphorous esters, and phosphoric acid amides.

3. A method according to claim 2, wherein the amount of said stabilizer is in the range of 0.0001 to 1% by weight based on the amount of said maleimide.

4. A method according to claim 1, wherein the molecular oxygen content in said gas phase is in the range of 0.1 to 10% by volume.

5. A method according to claim 1, wherein the temperature at which said maleimide is handled is not lower than the melting point of said maleimide and not higher than the sum of said melting point and 50° C.

6. A method according to claim 2, wherein said stabilizer is an alkyl-substituted hydroxybenzene.

7. A method according to claim 2, wherein said stabilizer is a thiodipropionic ester.

8. A method according to claim 2, wherein said stabilizer is a hindered phenol.

9. A method according to claim 2, wherein said stabilizer is at least one phosphorus compound selected from the group consisting of phosphoric esters, phosphorous esters, and phosphoric acid amides.

10. A method according to claim 9, wherein said phosphorus compound is at least one member selected from the group consisting of tris(2-chloroethyl) phosphate, tris-nonylphenyl phosphite, tristearyl phosphite, distearyl pentaerythritol diphosphite, and hexamethyl phosphoric triamide.

11. A method according to claim 2, wherein said stabilizer is a mixture consisting of at least one alkyl-substituted hydroxybenzene and at least one phosphorus compound selected from the group consisting of phosphoric esters, phosphorous esters, and phosphoric acid amides.

12. A method according to claim 11, wherein said alkyl-substituted hydroxybenzene is at least one member selected from the group consisting of 2,4-dimethyl-6-tert-butyl phenol, 4-tert-butyl catechol, 2,4-di-tert-butyl hydroquinone, 2-tert-butyl hydroquinone, 4,4'-thio-bis(6-tert-butyl-m-cresol), 2,4-bis(n-octylthio)-6-(4-hydroxy-3,5-di-t-butylanilino)-1,3,5-tiazine, 2,2'-thio-bis-(4-methyl-6-t-butylphenol), and triethylene glycol-bis-[3-(3-t-butyl-5-methyl-4-hydroxyphenyl)propionate].

13. A method according to claim 11, wherein said phosphorous ester and said phosphoric ester are at least one member selected from the group consisting of tris(-nonylphenyl) phosphite, tristearyl phosphite, distearyl pentaerythritol diphosphite, and tris(2-chloroethyl) phosphate.

14. A method for handling a maleimide, which method comprises melting said maleimide in the presence of a stabilizer at a temperature exceeding the melting point thereof in a state kept in contact with a gas phase having a molecular oxygen content of not more than 10% by volume, cooling the resultant molten maleimide until solidification, heating the solid maleimide in the presence of said stabilizer at a temperature exceeding said melting point in a state kept in contact with a gas phase having a molecular oxygen content of not smaller than 0.1% by volume, and handling the resultant liquid maleimide.

15. A method according to claim 14, wherein said stabilizer is at least one compound selected from the group consisting of alkyl-substituted hydroxybenzenes, thiodipropionic esters, hindered phenols, phosphoric esters, phosphorous esters, and phosphoric acid amides.

16. A method according to claim 14, wherein the amount of said stabilizer is in the range of 0.0001 to 1% by weight based on the amount of said maleimide.

17. A method according to claim 14, wherein the molecular oxygen content in said gas phase in either of said heat treatments is in the range of 0.1 to 10% by volume.

18. A method according to claim 14, wherein the temperature at which said maleimide is handled is not lower than the melting point of said maleimide and not higher than the sum of said melting point and 50° C.

19. A method according to claim 14 wherein said solid maleimide has been obtained by placing the maleimide in a liquid state in a hermetically sealable container said container being provided with a part to be heated, and then cooling said liquid maleimide until solidification.

* * * * *